US012758574B2

(12) United States Patent
Cox et al.

(10) Patent No.: US 12,758,574 B2
(45) Date of Patent: Oct. 13, 2026

(54) ANTIBIOTICS

(71) Applicant: ASTON UNIVERSITY, Birmingham (GB)

(72) Inventors: Jonathan Cox, Birmingham (GB); Nicolas Barry, Bradford (GB); James Harrison, Birmingham (GB); Victoria Nolan, Birmingham (GB); Anaïs Pitto-Barry, Bradford (GB); Joan Soldevila-Barreda, Bradford (GB)

(73) Assignee: Aston University, Birmingham (GB)

( * ) Notice: Subject to any disclaimer, the term of this patent is extended or adjusted under 35 U.S.C. 154(b) by 985 days.

(21) Appl. No.: 17/909,197

(22) PCT Filed: Feb. 24, 2021

(86) PCT No.: PCT/GB2021/050471
§ 371 (c)(1),
(2) Date: Sep. 2, 2022

(87) PCT Pub. No.: WO2021/176199
PCT Pub. Date: Sep. 10, 2021

(65) Prior Publication Data

US 2023/0090293 A1 Mar. 23, 2023

(30) Foreign Application Priority Data

Mar. 6, 2020 (GB) .................................... 2003320

(51) Int. Cl.
*A61K 31/7135* (2006.01)
*A61K 9/00* (2006.01)
*A61K 9/12* (2006.01)
*A61K 9/20* (2006.01)
*A61P 31/04* (2006.01)

(52) U.S. Cl.
CPC ........ *A61K 31/7135* (2013.01); *A61K 9/0019* (2013.01); *A61K 9/0048* (2013.01); *A61K 9/12* (2013.01); *A61K 9/20* (2013.01); *A61P 31/04* (2018.01)

(58) Field of Classification Search
CPC ................................................ A61K 31/7135
See application file for complete search history.

(56) References Cited

FOREIGN PATENT DOCUMENTS

| | | |
|---|---|---|
| CN | 110256502 A | 9/2019 |
| WO | 2013/033018 A2 | 3/2013 |
| WO | 2016/087932 A2 | 6/2016 |

OTHER PUBLICATIONS

International Search Report and Written Opinion received in PCT/GB2021/050471 mailed Apr. 30, 2021, 12 pages.
Bashari et al: "Synthesis, characterization, and antimicrobial activity of organometallic ruthenium(II) complexes", Journal of Undergraduate Chemistry Research, vol. 5, Jan. 1, 2006 (Jan. 1, 2006), pp. 99-104, XP055795667; XP009526966.
Neumann Bernd et al: "Synthesis, Structures and Comparison of Neutral Complexes Formed by2-(2'-Pyridyl) Indole and d6 Transition Metals", European Journal of Inorganic Chemistry, vol. 2007, No. 3, Jan. 1, 2007 (Jan. 1, 2007), pp. 472-480, XP055795498, DE ISSN: 1434-1948, DOI: 10.1002/ejic.200600730.
Ganesan Vinothkumar et al: "Correlation between the Structure and Catalytic Activity of [Cp*Rh(Substituted Bipyridine)] Complexes for NADH Regeneration", Inorganic Chemistry, vol. 56, No. 3, Jan. 10, 2017 (Jan. 10, 2017), pp. 1366-1374, XP055791251, Easton, US ISSN: 0020-1669, DOI: 10.1021/acs.inorgchem.6b02474 Retrieved from the Internet: URL:https://pubs.acs.org/doi/pdf/10.1021/acs.inorgchem.6b02474.
Corte-Real Leonor et al: "The key role of coligands in novel ruthenium(II)-cyclopentadienyl bipyridine derivatives: Ranging from noncytotoxic to highly cytotoxic compounds", Journal of Inorganic Biochemistry, Elsevier Inc, US, vol. 150, Jun. 20, 2015 (Jun. 20, 2015), pp. 148-159, XP029322862, ISSN: 0162-0134, DOI: 10.1016/J.JINORGBI0.2015.06.015.
Blakemore et al: "Half-Sandwich Iridium Complexes for Homogeneous Water-Oxidation Catalysis", Journal of the American Chemical Society, vol. 132, No. 45, Nov. 17, 2010 (Nov. 17, 2010), pp. 16017-16029, XP055065578, Issn: 0002-7863, DOI: 10.1021/ja104775j.
Communication pursuant to Article 94(3) EPC received in corresponding European Application No. 21709768.2 on Jul. 19, 2023.
Soldevila-Barreda, Joan J. et al: "Synthesis, Characterisation and In Vitro Anticancer Activity of Catalytically Active Indole-Based Half-Sandwich Complexes", Molecules, vol. 25, No. 19, Oct. 3, 2020 (Oct. 3, 2020), p. 4540, XP093062649, DE ISSN: 1433-1373, DOI: 10.3390/molecules25194540.

*Primary Examiner* — John S Kenyon
(74) *Attorney, Agent, or Firm* — Meunier Carlin & Curfman LLC

(57) ABSTRACT

The invention provides a compound of Formula (I) or a pharmaceutically acceptable salt; wherein L is a substituted or non-substituted aromatic ligand; Z is a halogen or coordinating ligand; M is a group 8 or group 9 transition metal selected from; Fe, Ru, Os, Co, Rh and Os; A and B are independently selected from a substituted or non-substituted indole or pyridine, may be the same or different and coordinate to the transition metal M through the nitrogen atom of the indole or pyridine. The compounds have been shown to have use against antibiotic-resistant bacteria. A further aspect of the invention is directed towards treating or preventing bacterial infections.

17 Claims, 8 Drawing Sheets

Figure 1:
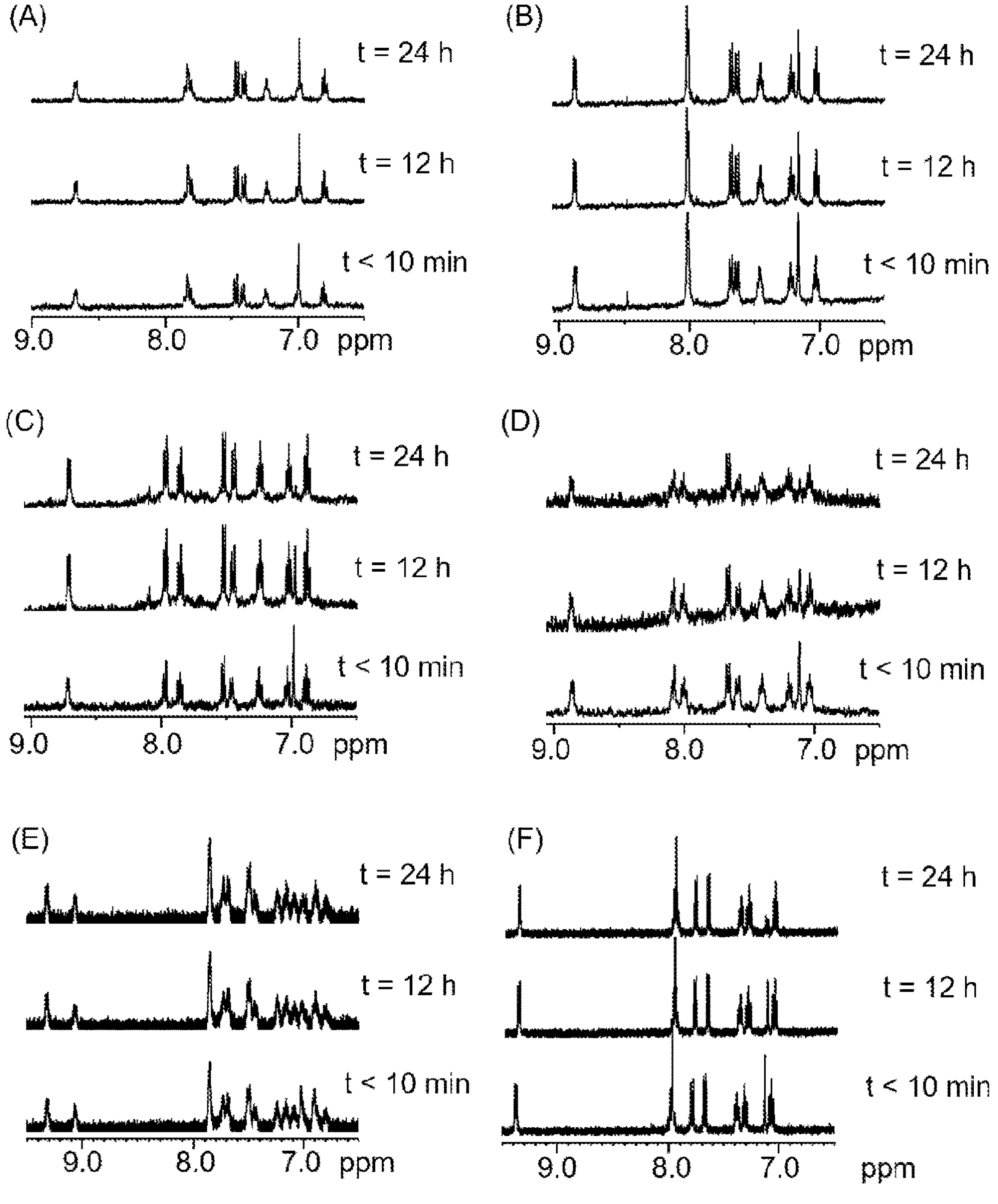

Figure 1: Stability of FKB10 in MeOD (A) and MeOD/$D_2O$ (B), FKB11 in MeOD (C) and MeOD/$D_2O$ (D) and FKB3 in MeOD (E) and MeOD/$D_2O$ (F).

ANTIBIOTICS

The invention relates to novel organometallic compounds, and their use as antibiotics, for example for the treatment of bacterial infections.

There is currently an urgent need for new antibiotics and strategies for treating drug-resistant bacterial infections. Bacterial resistance has developed against many, if not all, of current antibiotics. In the meantime, few antibiotics have being developed over the last number of decades. A primary cause of drug resistance is the over-use of antibiotics that can result in alteration of microbial permeability, alteration of drug target binding sites, induction of enzymes that destroy antibiotics (such as β-lactamases) and induction of efflux mechanisms.

The need for new antibiotics is even more urgent in the case of gram-negative bacteria such as *Pseudomonas, Klebsiella* and other bacteria such as *Escherichia* and *Acinetobacter.*

Many of the currently known antibiotics are structurally related to one another, and therefore are targets for drug resistance in bacteria. The inventors have unexpectedly identified a new class of organometallic compounds which have been found to have antibacterial properties.

The invention provides a compound of formula I for making

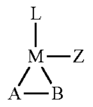

or a pharmaceutically acceptable salt; wherein L is a substituted or non-substituted aromatic ligand; Z is a halogen or coordinating ligand; M is a Group 8 or Group 9 transition metal selected from; Fe, Ru, Os, Co, Rh and Ir; A and B are independently selected from a substituted or non-substituted indole or pyridine, may be the same or different, and coordinate to the transition metal M through the nitrogen atom of the indole or pyridine.

The Group 8 metals may be $Fe^{II}$, $Ru^{II}$, or $Os^{II}$. The Group 9 metals may be $Co^{III}$, $Rh^{III}$, or $Ir^{III}$.

Components A and B are bound to the transition metal M through the nitrogen atom of the indole or pyridine and are additionally bound to one another by a bond, such as a carbon-carbon bond. That bond is typically between the carbons of each of A and B immediately adjacent to the nitrogen atom of the indole or pyridine. That is, carbon 2 or 6 of the pyridine or carbon number 2 of the indole group.

A and B may be the same, so may therefore be substituted or non-substituted indole, or substituted or non-substituted pyridine. More typically A and B are different, one being a substituted or non-substituted pyridine, the second being a substituted or non-substituted indole.

The indoles or pyridines may be functionalised with one or more substituents which will influence the lipophilicity of the resulting organometallic compound (e.g. sulfonic acid, benzene), have an effect on the electronic properties of the complexes (e.g. electron-deficient ligands such as carboranes), or bio-active ligands (e.g. sugars).

L may comprise one or two aromatic rings. The rings may be linked via a carbon-carbon bond for example, or may share a common bond. L may be a substituted or non-substituted cyclopentadienyl or a substituted or non-substituted benzene ring. Functionalisation of the ligand L may be performed to modify the chemical and physical properties of the resulting complexes, for example by introducing one or more side groups selected from a sugar, hydroxyl, halogen, carboxylate, amide, triazole or a $C_1$-$C_4$ straight or branched chain alkyl group. The halogen may be selected from, for example, chlorine, fluorine, bromine or iodine.

One or more active targeting moieties against bacteria may be connected to the aromatic ring via, for example, a carboxylate acid, amide or triazole group. The substitutions may be used to adjust the activity of the compound against the bacteria, alternatively, for example, adjust the solubility of the compound to allow the mode of administration to a subject to be optimised. One, two, three, four, five or all of the carbon atoms of the aromatic ring may be substituted.

L, A or B may be substituted by, for example, one or more methyl or $—CH(CH_3)_2$.

L may comprise a C5 or $C_6$ aromatic ring.

L may be selected from para-cymene, pentamethylcyclopentadiene, hexamethyl benzene, biphenyl and cyclopentadienyl.

M is typically selected from $Ru^{II}$, $Rh^{III}$, $Ir^{III}$ and $Os^{II}$.

Z is typically selected from a halogen or coordinating ligand compound wherein Z is preferably selected from Cl, Br, I, water, methanol, dimethyl sulfoxide, acetonitrile and dimethylformamide.

More preferably, the compound is selected from FKB3, FKB10 and FKB11.

FKB3

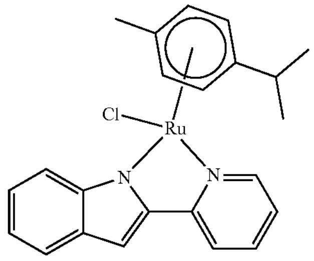

FKB10

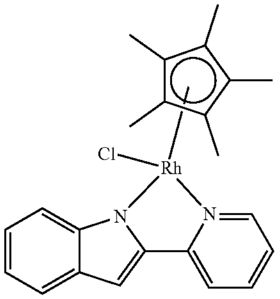

FKB11

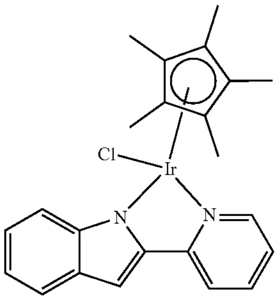

The chlorine atom of the compound may be replaced by one or more alternative halogen or coordinating ligands as defined above.

The invention also provides the compounds and pharmaceutically acceptable salts in combination with the pharmaceutically acceptable carrier. The carrier may, for example, be a solvent, such as an aqueous solvent, or alternatively a filler or bulking agent such as talc or carboxymethylcellulose.

The compound of pharmaceutically acceptable salt may be in a form suitable to be administered to a subject. These include, for example, oral tablets, oral suspensions, oral solutions, injectable formulations, such as intra-venously, intra-muscularly or intra-peritonealy, as eye drops or topical lotions or creams. The formulation may also be in a form suitable for administration through the nose or lungs, such as in the form of an aerosol.

Oral administration of compounds can be enclosed in hard or soft shell gelatine capsules, compressed into tablets or incorporated directly into the food of a patient's diet. Compounds can also be combined with one or more excipients and be used in the form of ingestible tablets, buccal tablets, troches, capsules, elixirs, suspensions, syrups, wafers and the like. Such compounds and preparations will typically contain at least 0.1% wt of active compound. The percentage of these compositions and preparations may vary depending on a given dosage form. Binders such as gum, tragacanth, acacia, corn starch or gelatine may be used. Excipients such as dicalcium phosphate, a disintegrating agent such as corn starch or potato starch, or a lubricant such as magnesium stearate may be used. Sweetening agents such as sugars or aspartame, or flavouring agents such as peppermint oil may be used. Additionally, when the dosage form is in the form of a capsule, a liquid carrier such as a vegetable oil or a polyethylene glycol may be used. Preservatives such as methyl and propyl parabens may be used together with one or more dyes or coatings, such as gelatine, wax, shellac and sugar or the like.

The subject to be treated may be a mammal, such as a human, but may also include cats, dogs, pigs, sheep, cows or rodents such as rats or mice.

The invention also provides a compound or pharmaceutically acceptable salt according to the invention, for use to treat or as prophylaxis for a bacterial infection. Methods for treating or prophylaxis of bacterial infections caused by a bacterium by administering to a subject an effective amount of a compound or pharmaceutically acceptable salt according to the invention is also provided.

A bacterial infection may be caused by a *Mycobacterium*, a Gram-positive bacterium or a Gram-negative bacterium, most typically a Gram-negative bacterium. The bacterium may be antibiotic resistant, for example by producing a beta-lactamase or carbapenumase.

Bacteria may be selected from the genus *Mycobacterium, Escherichia, Salmonella, Clostridium, Streptococcus, Staphylococcus, Pseudomonas, Klebsiella, Acinetobacter*, and *Enterobacter*, most preferably the bacterium is selected from *Mycobacterium abcsessus, Escherichia coli, Pseudomonas aeruginosa* or *Klebsiella pneumonia.*

A further aspect of the invention provides a method of killing or inhibiting the growth of a bacterium comprising contact of the bacterium with an effective amount of a compound of pharmaceutically acceptable salts according to the invention. The method may be in-vitro or in-vivo and may comprise a bacterium as defined above.

Figure 2:
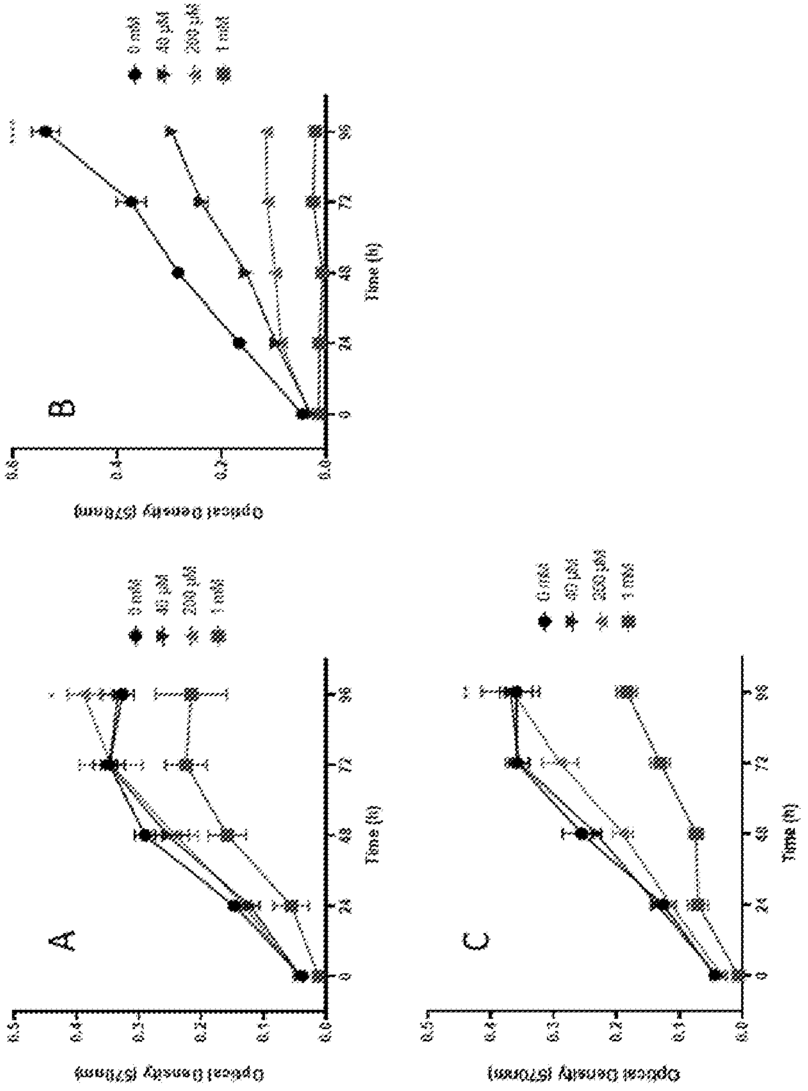
Figure 3:
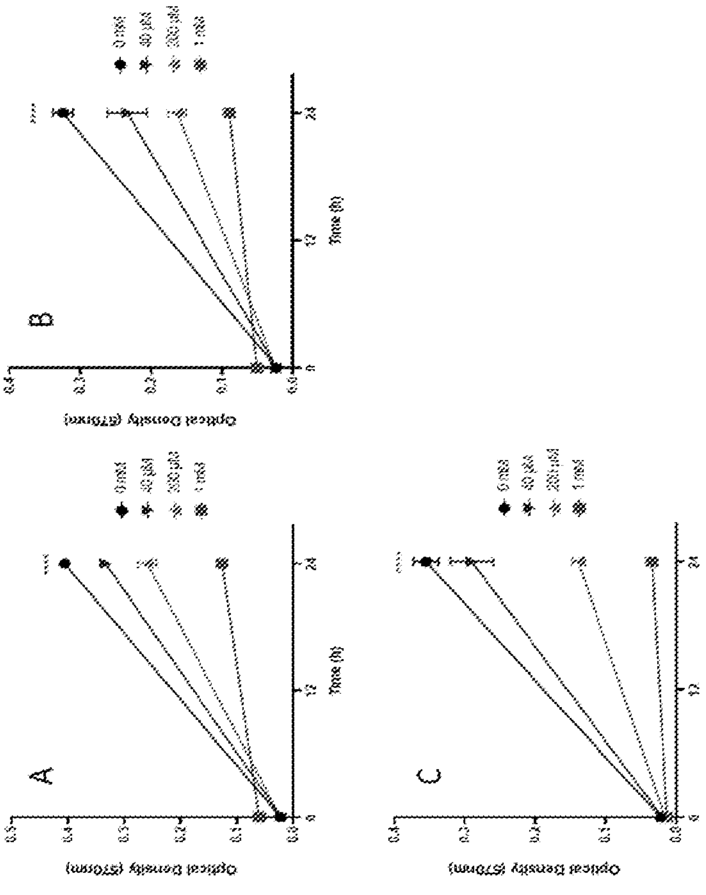
Figure 4:
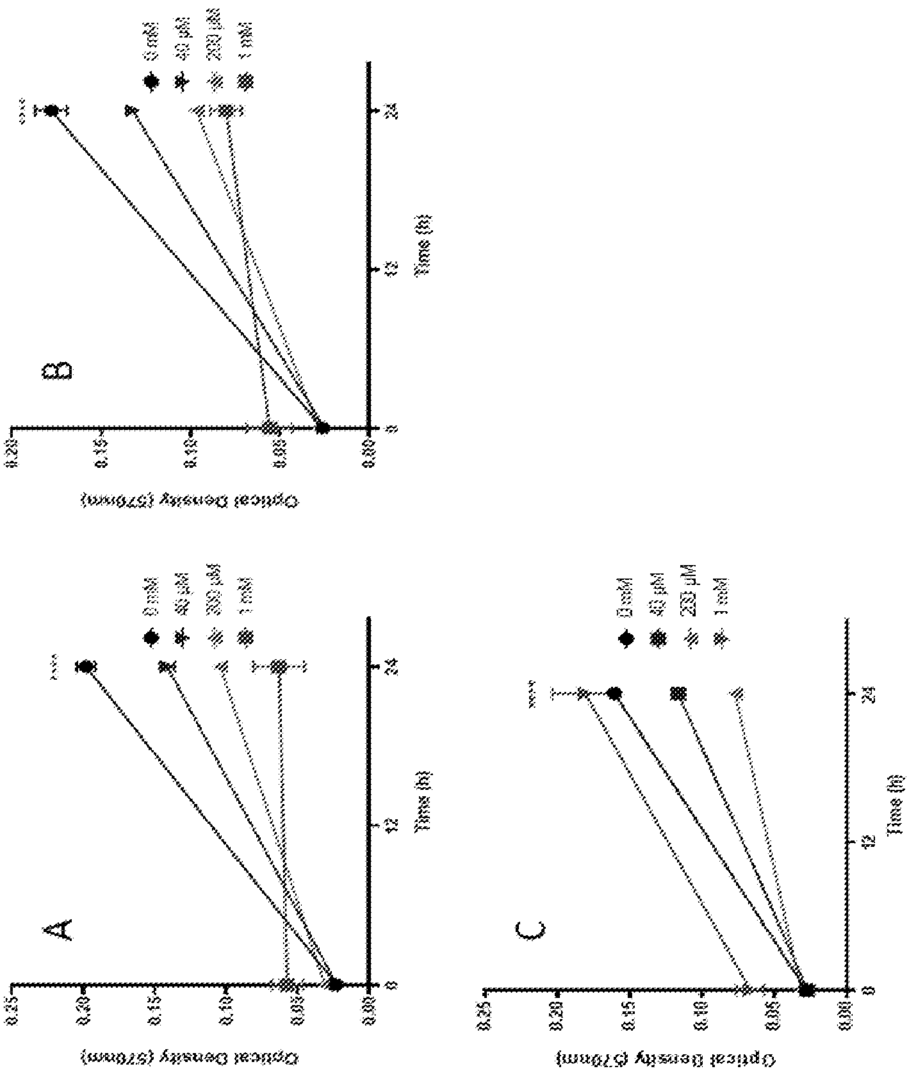
Figure 5:
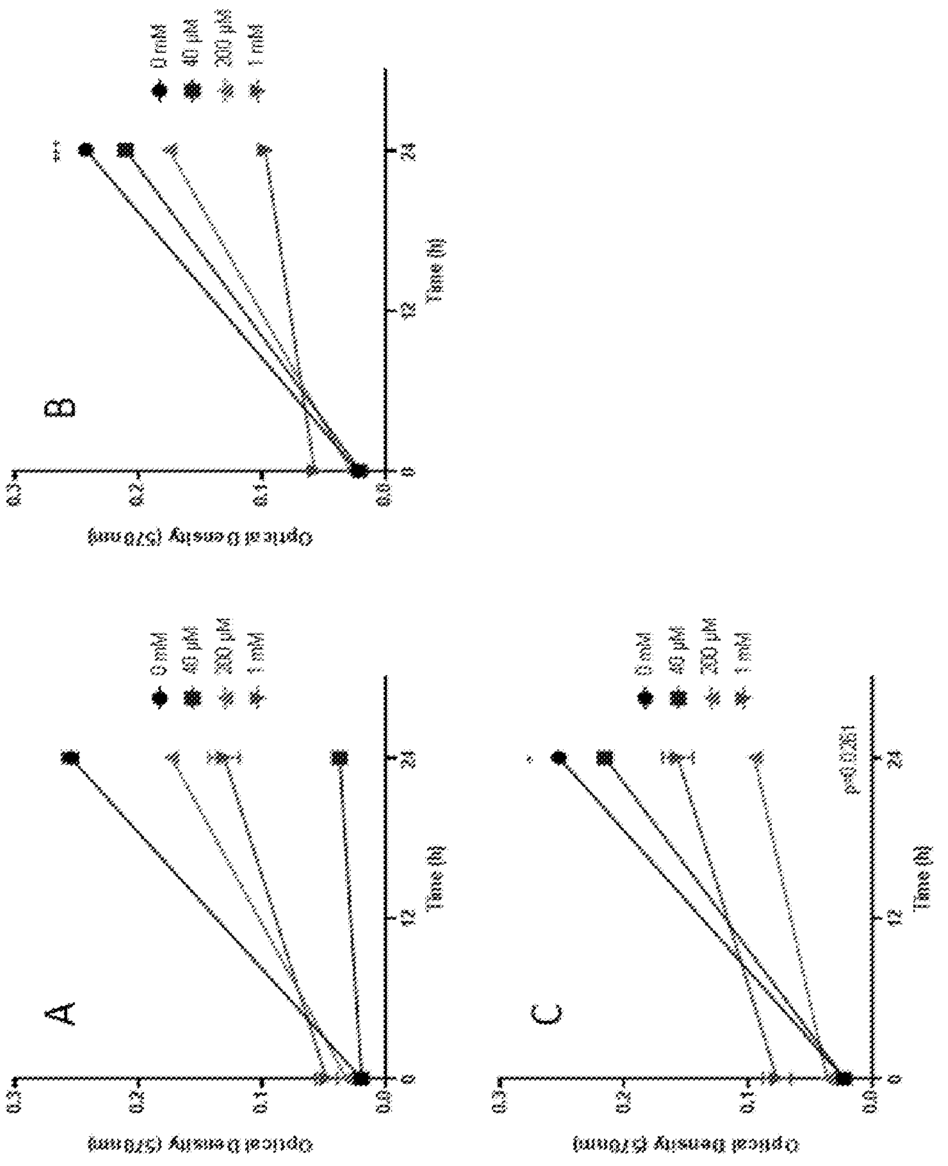
Figure 6:
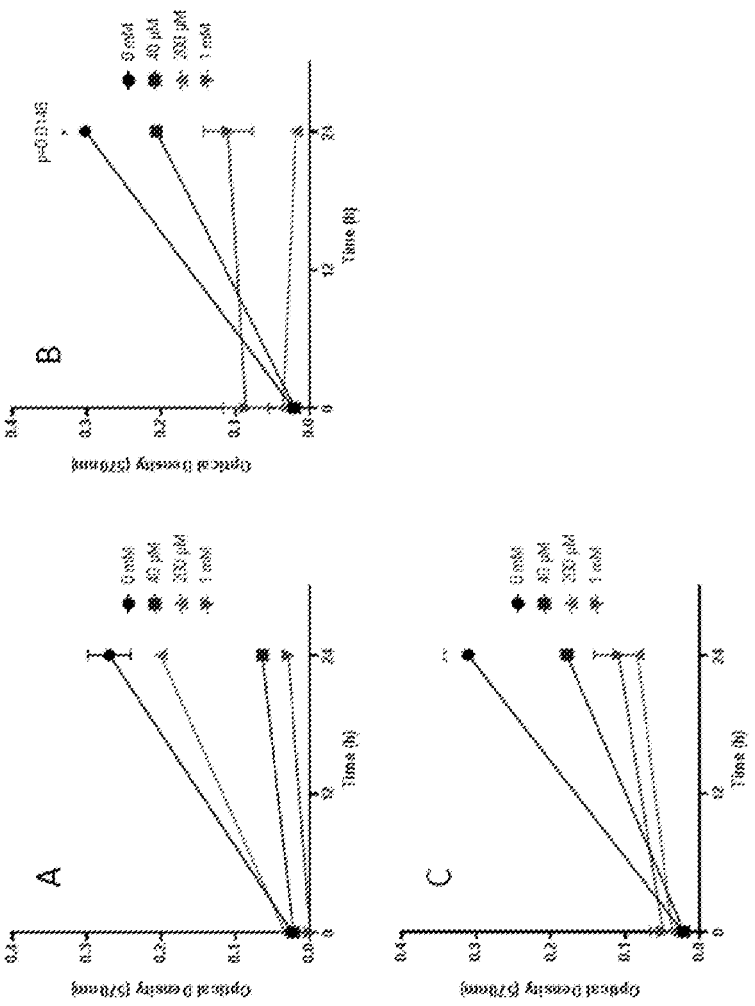
Figure 7:
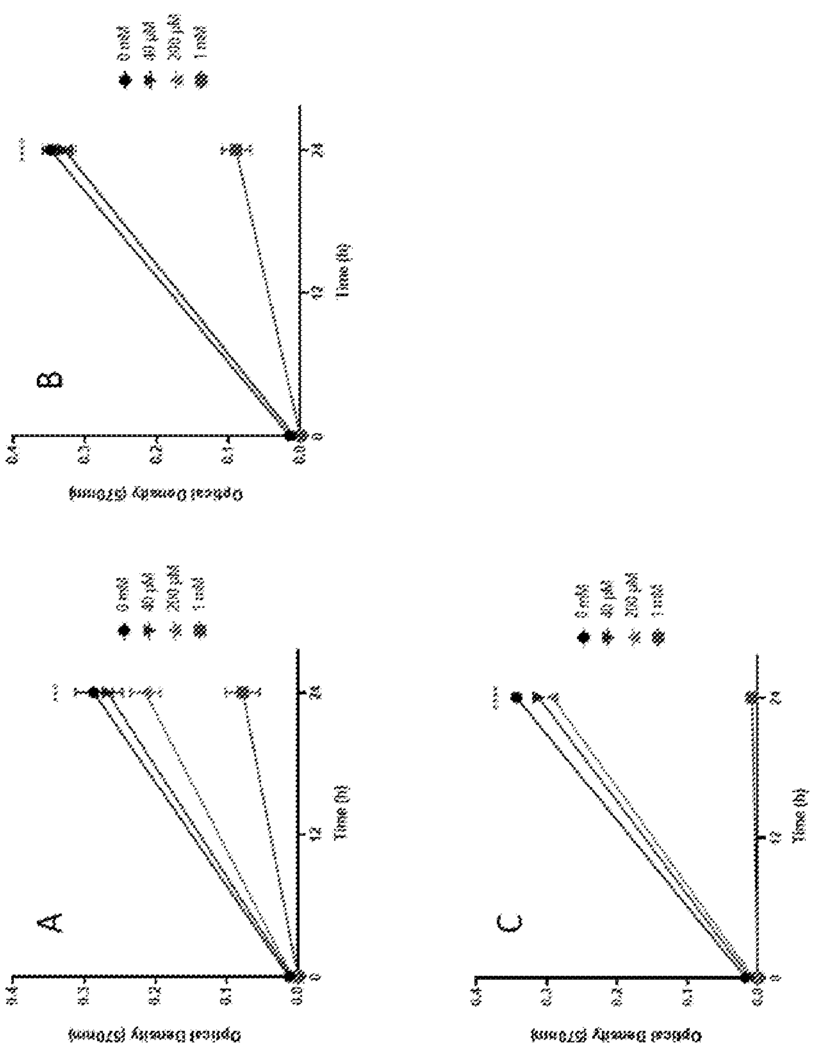
Figure 8:
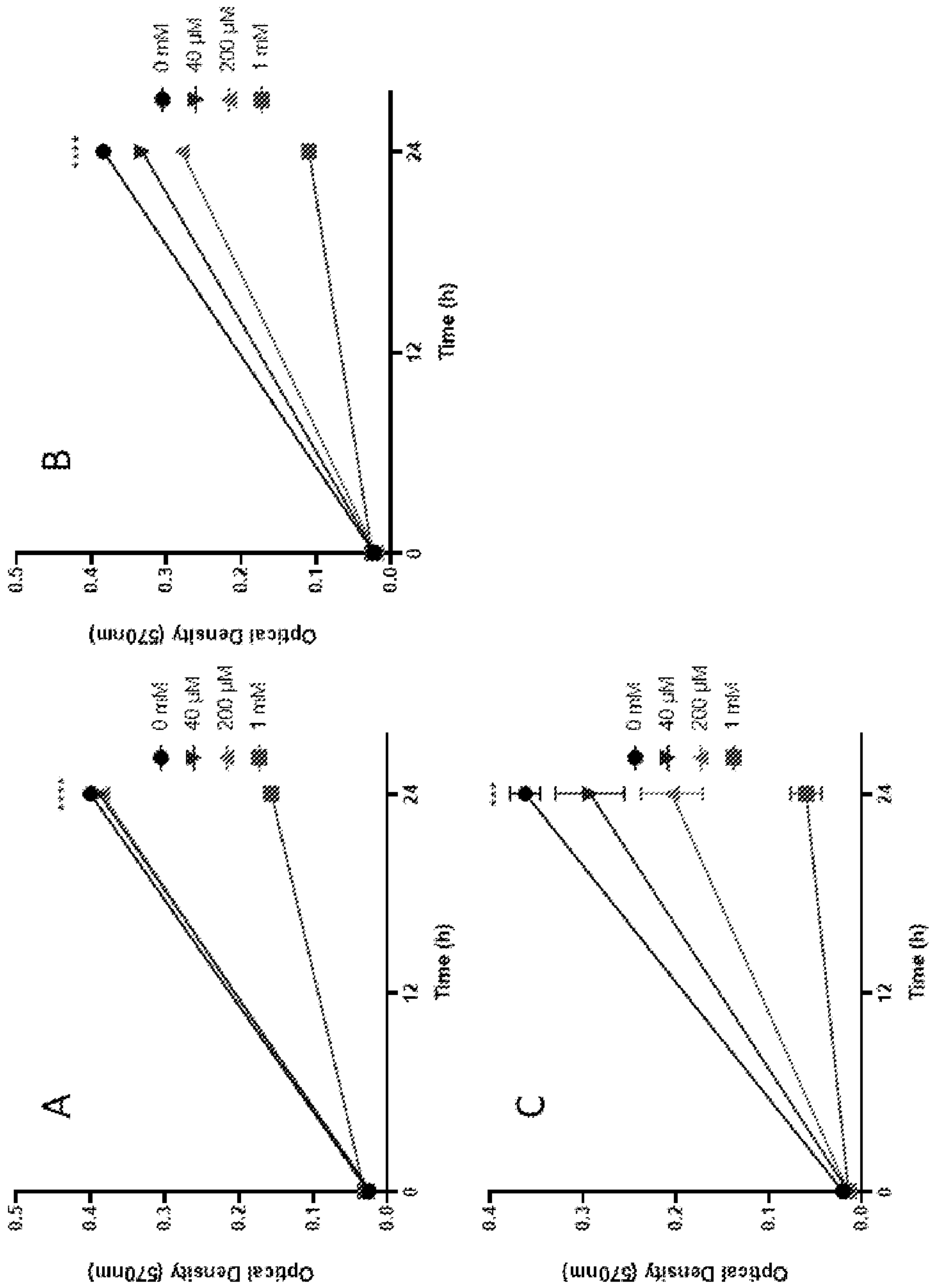

The invention will now be described by way of example only with reference to the following figures:

FIG. 1 provides stability of FKB10 in MeOD (A) and MeOD/$D_2O$(B), FKB11 in MeOD (C) and MeOD/$D_2O$ (D) and FKB3 in MeOD (E) and MeOD/$D_2O$ (F);

FIG. 2 start point and end point data for compounds tested against *M. abscessus* measured at 570 nm. A FKB3, B FKB10, C FKB11;

FIG. 3 start point and end point data for compounds tested against *E. coli* ATCC measured at 570 nm. A FKB3, FKB10, C FKB11;

FIG. 4 start point and end point data for compounds tested against *E. coli* J53 2138E measured at 570 nm. A FKB3, FKB10, C FKB11;

FIG. 5 start point and end point data for compounds tested against *E-coli* J53 2140E measured at 570 nm. A FKB3, B FKB10, C FKB11;

FIG. 6 start point and end point data for compounds tested against *E. coli* 1496 ESBL measured at 570 nm. A FKB3 B FKB10, C FKB11;

FIG. 7 start point and end point data for compounds tested against *P. aeruginosa* ATCC measured at 570 nm. A FKB3, B FKB10, C FKB11;

FIG. 8 start point and end point data for compounds tested against *K. pneumoniae* H467 measured at 570 nm. A FKB3, B FKB10, C FKB11.

1.1 Synthesis and Stability of FKB3, FKB10 and FKB11

FKB3: p-cymene ruthenium dimer (118.2 mg, 0.19 mmol) and 2-(2-pyrindyl)-1H-Indole (75 mg, 0.38 mmol) were placed in a 100 mL 2 neck round bottom flask and dissolved in 15 ml dichloromethane. Triethylamine (54 μl, 0.38) was added to the reaction mixture. The dark orange solution was then left stirring overnight at room temperature under nitrogen. The solvent was removed under vacuum. The orange crude was dissolved in ethyl acetate and washed with 0.1 M HCl (3×10 mL) and brine (1×10 mL). The combined organic layer was dried over $MgSO_4$, filtered and dried over vacuum to obtain an orange powder. The product was purified by chromatography (acetone/dichloromethane 10:90 v/v). Yield: 72.1 mg (40.2%). HRMS-ESI+: calculated $(M-Cl)^+$ 429.0905 m/z, found 429.0906 m/z. 1H NMR (400 MHz, $CDCl_3$): $\delta_H$ 8.94 ppm (1H, d, J=5.8 Hz), 7.73 (1H, d, J=8.2 Hz), 7.68 (1H, d, J=7.0 Hz), 7.63 (1H, d, J=8.2 Hz), 7.52 (1H, d, J=8.2 Hz), 7.15 (2H, t, J=7.5 Hz), 7.01 (3H, m), 5.95 (1H, d, J=6.1 Hz), 5.59 (1H, d, J=6.1 Hz), 5.53 (15H, s), 2.35 (1H, sept, J=6.9 Hz), 2.31v(3H, s), 0.88 (3H, d, J=6.9 Hz), 0.86 (3H, d, J=6.9 Hz).

FKB10: Rh dimer $[(Cp^*)RhCl_2]_2$ (110 mg, 0.18 mmol) and 2-(2-pyrindyl)-1H-Indole (78 mg, 0.38 mmol) were placed in a 2 neck round bottom flask and dissolved in 25 mL of dichloromethane to obtain an orange solution. Triethylamine (66 μL, 0.47 mmol) was added and the reaction mixture left to react for 24 h at room temperature. The solvent of the reaction mixture was removed under vacuum and the orange solid dissolved in dichloromethane (20 mL) and extracted with 0.1 M HCl solution (1×10 mL). The combined organic layer was dried over magnesium sulfate, filtered and dried over vacuum to obtain an orange powder. The product was purified by column chromatography in silica, acetone/dichloromethane (1:9 v/v) and recrystallised in dichloromethane to obtain crystalline orange needles. Yield: 63.4 mg (38.1%). HRMS-ESI+: calculated $(M-Cl)^+$ 431.1000 m/z, found 431.0833 m/z. 1H NMR (400 MHz, $CDCl_3$): $\delta_H$ 8.56 ppm (1H, d, J=5.7 Hz), 7.74 (1H, d, J=8.2 Hz), 7.68 (1H, t, J=7.8 Hz), 7.61 (1H, d, J=7.8 Hz), 7.46 (1H, d, J=8.2 Hz), 7.08 (2H, m), 7.03 (1H, s), 6.93 (1H, t, J=7.6 Hz), 1.66 (15H, s).

FKB11: FKB11 was synthesised following the preparation described for compound FKB10 with the following modifications. Ir dimmer $[(Cp^*)IrCl_2]_2$ (102 mg, 0.128 mmol), 2-(2-pyrindyl)-1H-Indole (50 mg, 0.257 mmol). The product was obtained as a yellow powder. Yield: 64.5 mg (27.2%). HRMS-ESI+: calculated $(M-Cl)^+$ 521.1569 m/z, found 521.1564 m/z. 1H NMR (400 MHz, $CDCl_3$): $\delta_H$ 8.55 ppm (1H, d, J=5.6 Hz), 7.80 (1H, d, J=8.3 Hz), 7.67 (1H, t, J=7.8 Hz), 7.59 (1H, d, J=7.8 Hz), 7.44 (1H, d, J=8.5 Hz), 7.05 (2H, m), 6.94 (1H, m), 1.66 (15H, s).

Stability of FKB3, FKB10 and FKB11: Each complex was dissolved in MeOD (2.2 mM) and diluted to a final concentration of 1.1 mM with either MeOD or $D_2O$. $^1H$ NMR spectra was recorded at t=<10 min, 12 h and 24 h.

Each complex was also dissolved in MeOD (2.2 mM) and diluted to a final concentration of 1.1 mM with $D_2O$. The sample was then reacted with 1 mol. equiv. of silver nitrate to obtain the fully hydrolyzed specie.

From the NMR spectra of FIG. 1 it can be observed that FKB10 is stable over 24 h both in methanol and in aqueous solution. Furthermore, addition of silver nitrate does not produce any shift of the $^1H$ NMR resonances, suggesting that ligand substitution occurs replacing the chloride ligand by either methanol or water.

The iridium compound FKB11 shows no changes in the $^1H$ NMR spectra, which indicates stability; as a side note, the compound is quite insoluble, and it precipitates over time. The ruthenium complex FKB3 is fully stable. Interestingly, when the compound is dissolved in 100% MeOD, two species can be observed, corresponding to the chloride and the methoxide adducts.

FIG. 1: Stability of FKB10 in MeOD (A) and MeOD/$D_2O$ (B), FKB11 in MeOD (C) and MeOD/$D_2O$ (D) and FKB3 in MeOD (E) and MeOD/$D_2O$ (F).

1.2. Chemosensitivity Assays Against Human Cell Lines

In vitro chemosensitivity tests were performed against HCT116 (colorectal cancer cell line), A2780 and A2780cisR (cisplatin sensitive and cisplatin resistant ovarian cancer cell lines, respectively). Cancer cell lines were routinely maintained as monolayer cultures in RPMI medium supplemented with 10% foetal calf serum, penicillin (100 I.U./ml) and streptomycin (100 μg/ml), sodium pyruvate (1 mM) and L-glutamine (2 mM). For chemosensitivity studies, cells were incubated in 96-well plates at a concentration of $7.5\times10^3$ cells per well and the plates were incubated for 24 hours at 37° C. and a 5% CO2 humidified atmosphere prior to drug exposure.

Complexes were dissolved in dimethylsulfoxide (DMSO) to provide stock solutions which were further diluted with media to provide a range of final concentrations. Drug-media solutions were added to cells (the final concentration of DMSO was less than 0.5% (v/v) in all cases) and incubated for 24 hours at 37° C. and 5% $CO_2$ humidified atmosphere. The drug-media was removed from the wells and the cells were washed with PBS (100 μL, twice), and 200 μL of complete fresh media were added to each well. The plates were further incubated for 72 hours at 37° C. in a humidified atmosphere of 5% CO2 to allow for a period of recovery. 3-(4,5-dimethylthiazol-2-yl)-2,5-diphenyltetrazolium bromide (MTT) (40 μL, 2.5 mg/mL) was added to each well and incubated for 2 hours at 37° C. and 5% $CO_2$ humidified atmosphere. All solutions were then removed and 100 μL of DMSO was added to each well in order to dissolve the purple formazan crystals. A Thermo Scientific Multiskan EX microplate photometer was used to measure the absorbance in each well at 570 nm. Cell survival was determined as the absorbance of treated cells divided by the absorbance of controls and expressed as a percentage. The $IC_{50}$ values were determined from plots of % survival against drug concentration. Each experiment was repeated in duplicate of triplicates and a mean value was obtained and stated as $IC_{50}$ (μM)±SD. Cisplatin was used as a positive control. As a side note, the higher the $IC_{50}$ values are, the less cytotoxic the compounds are.

TABLE 1

$IC_{50}$ values/μM ± SD for cisplatin and compounds FKB3, FKB10, and FKB11 against HCT116, A2780, and A2780 cell lines.

| | | $IC_{50}$/μM ± SD | | |
|---|---|---|---|---|
| Complex | Metal | HCT116 | A2780 | A2780cisR |
| FKB3 | Ru | 107.9 ± 11.5 | 45.4 ± 6.9 | 71.9 ± 11.7 |
| FKB10 | Rh | 104.2 ± 9.8 | 23.5 ± 1.3 | 41.0 ± 4.7 |
| FKB11 | Ir | 64.81 ± 4.6 | 22.2 ± 2.1 | 32.6 ± 1.7 |
| cisplatin | Pt | 59.8 ± 7.5 | 5.7 ± 0.4 | 11.9 ± 2.2 |

2. Antimicrobial Activity 2.1 Methods

Growth of Organisms

All *Mycobacterium abscessus* (*M. abs*) cultures were grown in Middlebrook 7H9 media, supplemented with glycerol (0.5% v/v), ADC (acid-dextrose-glucose) (10% v/v) and tween80 (0.05% w/v), at 30° C. with shaking at 180 rpm for 72 h. The optical density ($OD_{600\ nm}$) was adjusted to 0.1 prior to microtiter plate set-up.

The gram negative organisms selected were *Escherichia coli* (*E. coli* ATCC, J53 2138E, J53 2140E and 1496 ESBL), *Pseudomonas aeruginosa* ATCC and *Klebsiella pneumoniae* H467. All organisms were grown in nutrient broth at 37° C. with 180 rpm shaking, for 18 h. The optical density ($OD_{600\ nm}$) was adjusted to 0.1 prior to microtiter plate set-up.

*M. abscessus* is an example of a *mycobacterium* capable of causing lung infections. J53 2138 E, J532140 E and I496ESBL are β-lactamase producing strains. H467 produces a carbapenumase.

Compounds

Each compound was made in DMSO (dimethyl sulfoxide) to a stock concentration of 100 mM. A master plate was used to generate the desired concentrations for testing. This was achieved by serial 5-fold dilution (repeated 5 times, the final row was DMSO only (0 mM)).

Experimental Set-up

For each compound, 95 μl of culture (OD 0.1) was added to the microtiter plate and 5 μl of serially diluted compound added. The concentrations tested were: 1 mM, 200 μM, 40 μM, 8 μM, 1.6 μM and 320 nM. All plates were read in the plate reader at 570 nm (T=0). For *M. abs* the plates were incubated at 30° C. for 96 h with reads being taken every 24 h. For gram negative organisms the plates were incubated at 37° C. and read at 0 h and 24 h. After the final read for all organisms the experiment was plated out to observe bactericidal activity. *M. abs* was plated onto Middlebrook 7H11 agar supplemented with glycerol (0.5%) and incubated at 30° C. for 72-96 h. The gram negative organisms were plated onto nutrient agar and incubated at 37° C. for 24 h. Colony forming units were counted for all organisms.

Data Analysis

All OD readings were transferred to excel and adjusted to account for OD of the broth and compounds. The data was then transferred to GraphPad Prism 8 for data analysis.

2.2 Results

Out of the compounds tested, activity was observed for a total of 5 compounds. Three of the compounds, FKB3, FKB10 and FKB11, exhibited varying levels of growth inhibition against all organisms tested.

*M. abscessus* ATCC

Reduction in optical density reading was observed for all compounds tested against *M. abs* at 1 mM (FIG. 2). Uniquely, FKB10 showed a further reduction in optical density at both 200 μM and 40 μM, suggesting the highest potency against *M. abs* (FIG. 2B).

*E. coli* ATCC

All compounds tested against *E. coli* ATCC showed activity down to 40 μM (FIG. 3). Both FKB10 and FKB11 were the most potent, showing the least change in optical density over 24 h at 1 mM concentration (FIG. 3B/C). FKB3 and FKB11 both have minimum bactericidal concentrations (MBC) of 1 mM.

*E. coli* J53 2138

All of compounds tested against *E. coli* J53 2138E showed a reduction in optical density. FKB3 and FKB11 were the only compounds with an observable MBC of 1 mM respectively.

*E. coli* J53 2140E

All of the compounds tested show a reduction of optical density over 24 h, with the largest reduction in change of optical density seen for FKB11 at 200 μM (FIG. 5C). FKB3 and FKB11 were the only compounds with an observable MBC of 1 mM respectively.

*E. coli* 1496 ESBL

All of the compounds tested show a reduction of optical density over 24 h, with the largest reduction in change of optical density seen for FKB3 at 1 mM, as well as FKB10 at 200 μM (FIG. 6A/B). FKB3 and FKB11 were the only compounds with an observable MBC of 1 mM respectively.

*P. aeruginosa* ATCC

All of the compounds tested caused a reduction in change of optical density at 1 mM (FIG. 7). The largest of these reductions occurred when *P. aeruginosa* was treated with FKB11 (FIG. 7C). However, despite this, there was no observable MBC for any compound against *P. aeruginosa*, suggesting these compounds are bacteriostatic, rather than bactericidal against this organism.

*K. pneumoniae* H467

Each compound tested against *K. pneumoniae* H467 showed a reduction in optical density over 24 h. The largest reduction occurred with the addition of FKB11 at 1 mM (FIG. 8C). Both FKB3 and FKB11 gave an MBC of 1 mM.

CONCLUSIONS

These compounds show activity against a wide range of bacterial species, including highly antimicrobial Gram negative strains. Although the optimal concentration for activity is high (1 mM), a number of these compounds are bactericidal against the majority of the organisms screened. Therefore, these compounds represent an intriguing avenue for use and future optimisation and drug development.

The invention claimed is:

1. A method of treating or prophylaxis of a bacterial infection caused by a bacterium comprising administering to a subject an effective amount of a compound or pharmaceutically acceptable salt of a compound of Formula I:

Formula I

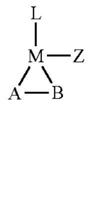

wherein L is a substituted or non-substituted aromatic ligand; Z is a halogen or coordinating ligand; M is a group 8 or group 9 transition metal selected from; Fe, Ru, Os, Co, Rh or Ir; A and B are independently selected from a substituted or non-substituted indole or pyridine, may be the same or different and coordinate to the transition metal M through the nitrogen atom of the indole or pyridine.

2. The method of treating or prophylaxis of claim 1, wherein one of A or B is a substituted or non-substituted indole; and the second of B or A is a substituted or non-substituted pyridine.

3. The method of treating or prophylaxis of claim 1, wherein L comprises 1 or 2 aromatic rings.

4. The method of treating or prophylaxis of claim 1, wherein L is a substituted or non-substituted cyclopentadienyl ring or a substituted or non-substituted benzene.

5. The method of treating or prophylaxis of claim 1, wherein L is substituted by one or more side groups comprising a sugar, hydroxyl, halogen, carboxylate, triazole, amide or a $C_1$ to $C_4$ straight or branched chain alkyl group.

6. The method of treating or prophylaxis of claim 1, wherein L is selected from para-cymene, pentamethylcyclopentadienyl, hexamethyl benzene, biphenyl or cyclopentadienyl.

7. The method of treating or prophylaxis of claim 1, wherein the compound of Formula I is selected from FKB3, FKB10 or FKB11:

FKB3

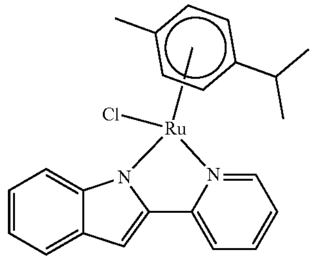

FKB10

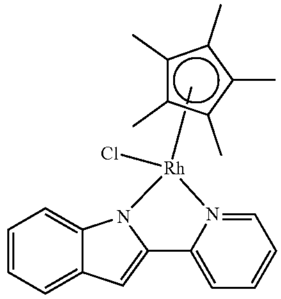

-continued

FKB11

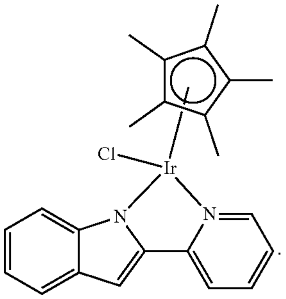

8. The method of treating or prophylaxis of claim 1 wherein the bacterial infection is caused by a *Mycobacterium*, a Gram-positive bacterium or a Gram-negative bacterium.

9. The method of treating or prophylaxis of claim 1 wherein the bacterium is antibiotic resistant.

10. The method of treating or prophylaxis of claim 1, wherein the bacterium produces a β-lactamase or carbapenumase.

11. The method of treating or prophylaxis of claim 1, wherein the bacterium is from the genus *Mycobacterium, Escherichia, Salmonella, Clostridium, Streptococcus, Staphylococcus, Pseudomonas, Klebsiella, Acinetobacter* or *Enterobacter.*

12. The method of treating or prophylaxis of claim 1, wherein the bacterium is *Mycobacterium absessus*, or *Escherichia coli, Pseudomonas aeruginosa*, or *Klebsiella pneumonia.*

13. A compound of Formula I

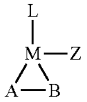

or a pharmaceutically acceptable salt; wherein L is a substituted or non-substituted aromatic ligand; Z is a halogen or coordinating ligand; M is a group 8 or group 9 transition metal selected from; Fe, Ru, Os, Co, Rh or Ir; A and B are independently selected from a substituted or non-substituted indole or pyridine, may be the same or different and coordinate to the transition metal M through the nitrogen atom of the indole or pyridine; in combination with a pharmaceutically acceptable carrier.

14. The compound or pharmaceutically acceptable salt of claim 13, selected from FKB3, FKB10 or FKB11

FKB3

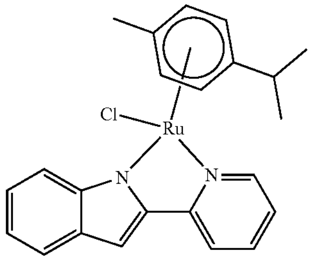

FKB10

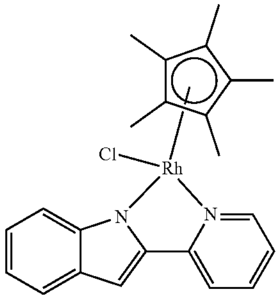

FKB11

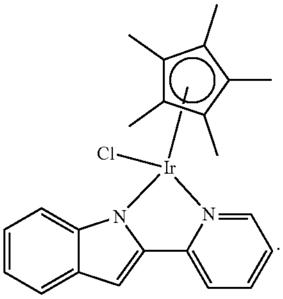

15. The compound or pharmaceutically acceptable salt of claim 13 in the form of an oral tablet, an oral suspension and solution, an injectable formulation, eye drops, a topical lotion, a topical cream or an aerosol.

16. A method of killing or inhibiting the growth of a bacterium comprising contacting the bacterium with an effective amount of the compound or pharmaceutically acceptable salt of claim 13.

17. The method of treating or prophylaxis of claim 2, wherein one of A or B is a non-substituted indole; and the second of B or A is a non-substituted pyridine.

* * * * *